United States Patent [19]

Hou

[11] Patent Number: 5,908,628

[45] Date of Patent: Jun. 1, 1999

[54] COMPOSITIONS WITH ANALGESIC, ANTIPYRETIC AND ANTIINFLAMMATORY PROPERTIES

[76] Inventor: Liping Hou, 300 Jingzhou Wan Road, Taiyuan, Shanxi Province, China

[21] Appl. No.: 09/070,240

[22] Filed: May 1, 1998

[51] Int. Cl.⁶ .............................. A01N 65/00; A61K 35/24
[52] U.S. Cl. ....................... 424/195.1; 424/537; 514/825; 514/886; 514/916
[58] Field of Search ................................. 424/195.1, 537, 424/520, 489; 514/916, 886, 887, 825

[56] References Cited

U.S. PATENT DOCUMENTS

| 5,417,979 | 5/1995 | Fan et al. | 424/451 |
| 5,466,452 | 11/1995 | Whittle | 424/195.1 |
| 5,595,743 | 1/1997 | Wu | 424/195.1 |
| 5,627,195 | 5/1997 | Hu | 514/321 |

FOREIGN PATENT DOCUMENTS

| 1101577 | 4/1995 | China . |
| 62-175476 | 8/1987 | Japan . |

OTHER PUBLICATIONS

Sugishita, E. et al., J. Pharm. Dyn., vol. 5(6), pp. 379–387, 1982.

Koo Dong Ham et al., J. of the Pharmaceutical Society of Korea, vol. 19(3), pp. 129–155, 1975.

*Primary Examiner*—Francisco Prats
*Assistant Examiner*—Kristin K. Vidovich
*Attorney, Agent, or Firm*—Morgan, Lewis & Bockius LLP

[57] ABSTRACT

The present invention provides compositions comprising talc, silkworm excrement, and ingredients of plants of species of the genera Stephania, Coix, Pinellia, Prunus, Phellodendron, Sophora, Tetrapanax, Stemona, Glycyrrhiza, Tripterygium, Forsythia and Siegesbeckia, wherein such compositions have analgesic, antipyretic, and antiinflammatory properties. The present invention also provides methods of using such compositions for treating various diseases, including osteoarthritis and rheumatoid arthritis.

17 Claims, No Drawings

5,908,628

COMPOSITIONS WITH ANALGESIC, ANTIPYRETIC AND ANTIINFLAMMATORY PROPERTIES

FIELD OF THE INVENTION

The present invention pertains, in general, to the field of therapeutic compounds for the treatment of pain, fever and inflammation. In particular, the present invention pertains to compositions comprising talc, silkworm excrement and various herbs, wherein such compositions are useful for the treatment of rheumatoid and/or arthritic conditions.

BACKGROUND OF THE INVENTION

All publications and patent applications herein are incorporated by reference to the same extent as if each individual publication or patent application was specifically and individually indicated to be incorporated by reference.

Rheumatism refers to any of several pathological conditions of the muscles, tendons, joints, bones, or nerves, characterized by discomfort and disability. It is estimated that over 100 rheumatic diseases affect the joints and other connective tissues of animals.

Arthritis generally refers to the inflammation of a joint or joints which results in pain and swelling. The two most common forms of arthritis are osteoarthritis and rheumatoid arthritis. Osteoarthritis is characterized by chronic degeneration of the cartilage of the joints, mainly in older persons. Rheumatoid arthritis, sometimes called arthritis deformans, is a chronic and progressive systemic disease, especially common in women, characterized by stiffness, swelling and inflammation of the joints and sometimes leading to deformity and permanent disability. Sufferers of rheumatoid arthritis may also have general symptoms of fatigue, weakness, and loss of appetite. While there is no cure, these diseases can sometimes be managed by lifestyle and diet changes.

Many other diseases also cause pain, inflammation and fevers. Rheumatic fever is an acute inflammatory disease occurring during recovery from infection with group A streptococci, having an onset marked by fever and joint pain. It is associated with polyarthritis, Sydenham's chorea, and endocarditis, and is frequently followed by scarring of the heart valves. Lupus erythematosus, also known as systemic lupus erythematosus, is a chronic disease of unknown origin characterized by red, scaly lesions or patches on the face and upper portion of the trunk. Erythema nodosum is a skin disease associated with joint pain, fever, hypersensitivity, or infection, and characterized by small, painful, pink to blue nodules under the skin and on the shins that tend to recur. Gout is an inherited disorder of uric-acid metabolism occurring predominantly in men, characterized by painful inflammation of the joints, especially of the feet and hands, and arthritic attacks resulting from elevated levels of uric acid in the blood and the deposition of urate crystals around the joints. The condition can become chronic and result in deformity.

When diet and lifestyle changes are not sufficient to alleviate the symptoms of rheumatism and rheumatoid-like diseases, pharmaceuticals are often used for relief from the resultant pain, discomfort, and fever. The antiinflammatory, analgesic and antipyretic agents and drugs often employed for this purpose are a heterogeneous group of compounds; often chemically unrelated, which nevertheless share certain therapeutic actions and side effects. For a comprehensive discussion of such drags see Insel, P. A., *Analgesic-Antipyretic and Antiinflammatory Agents and Drugs Employed in the Treatment of Gout,* In Goodman & Gilman's The Pharmacological Basis of Therapeutics, Ninth Edition, Chapter 27 (1996).

Herbal Medicines

It is estimated that approximately 50 percent of the thousands of drugs commonly used and prescribed today are either derived from a plant source or contain chemical imitations of a plant compound (Mindell, E. R., *Earl Mindell's Herb Bible,* A Fireside Book (1992)). Currently, a number of medicinal formulations contain herbal components or extracts from herbs. Technically speaking an herb is a small, non-woody (i.e., fleshy stemmed), annual or perennial seed-bearing plant in which all the aerial parts die back at the end of each growing season. As the word is more generally used and as it is used herein, an herb is any plant or plant part which has a medicinal use. Thus, the term herb is also generally used to refer to the seeds, leaves, stems, flowers, roots, berries, bark, or any other plant parts that are used for healing.

Herbal medicines have been used for treating various diseases of humans and animals in many different countries for a very long period of time (see, e.g., Kessler et al., *The Doctor's Complete Guide to Healing Medicines,* Berkley Health/Reference Books (1996); Mindell, supra). Herbal medications are available in many forms, including capsules, tablets, or coated tablets; pellets; extracts or tinctures; powders; fresh or dried plants or plant parts; prepared teas; juices; creams and ointments; essential oils; or, as combinations of any of these forms. Herbal medicines are administered by any one of various methods, including orally, rectally, parenterally, enterally, transdermally, intravenously, via feeding tubes, and topically.

The bark of the willow tree has been used to treat fever since the mid-eighteenth century in England. The active ingredient in willow bark is a bitter glycoside called salicin, which on hydrolysis yields glucose and salicylic alcohol. Aspirin (acetylsalicylic acid) and aspirin-like drugs (e.g., ibuprofen), all of which are often called nonsteroidal antiinflammatory drugs (NSAIDs), are frequently used to treat pain, fever, and inflammation. Meadowsweet is another herb that contains salicylates. Treatment of arthritic and arthritic-like symptoms with willow bark or meadowsweet requires the consumption of prohibitively large quantities of herbal teas made from these plants. The entire Populus species (i.e., poplar trees and shrubs) also contains salicylate precursors and poplar-buds have been used in antiinflammatory, antipyretic and analgesic medications.

While preliminary evidence suggests that joint inflammation may be reduced by the intake of plants which contain gamma-linolenic acid (e.g., black currant, borage, evening primrose), relief using these plants also requires the intake of large amounts of plant material. The alkaloid colchicine is extracted from the corm and the seeds of autumn crocus (*Colchicum autumnale*) and used in either tablet form or intravenously for patients with gout. Colchicine is also used to treat familial Mediterranean fever. However, as little as 7 mg of colchicine has been found to be fatal, although the normal fatal dose is 65 mg. European goldenrod (*Solidago virgaurea*) has been used to treat arthritis, kidney inflammation, and as a headache remedy for treating flu, sore throat, malaria and measles. Modern research has found that licorice (*Glycyrrhiza glabra*), which contains a medically active terpene component, can reduce arthritic activity. However, the cortisone-like component of the saponin like glycoside glycyrrhizin causes dangerous side effects, including abnormal heart action and kidney failure, triggered by potassium depletion. While alfalfa, black cohosh, blue-green algae, bog bean, burdock root, celery seeds, chaparral, comfrey, dandelion, devil's claw, feverfew, fresh ginger, juniper, mustard, parsley, sassafras, valerian, wormwood and yucca have all been reputed to bring relief of arthritis, there is little or no scientific evidence to support such assertions. For a more complete discussion of herbal-based medicines see Mindell, supra; *Culpeper's Complete Herbal,* W. Foulsham & Co., Ltd. (originally published in the mid 1600's); and, *Rodale's Illustrated Encyclopedia of Herbs,* Rodale Press (1987).

U.S. Patents have been issued for herbal medicinals used for the treatment of various diseases and other health-related problems afflicting humans and animals. For example, U.S. Pat. No. 5,417,979 discloses a composition comprising a mixture of herbs, including species of Stephania and Glycyrrhiza, as well as their extracts, which is used as an appetite stimulant and for the treatment of pain. Herbal compositions which include *Glycyrrhiza uralensis* have been found useful for treating eczema, psoriasis, pruritis and inflammatory reactions of the skin (U.S. Pat. No. 5,466, 452). U.S. Pat. No. 5,595,743 discloses various herbal compositions which include licorice extract (Glycyrrhiza) and siegesbeckia, sophora, stemona and tetrandra herbs used for the treatment of various mammalian diseases, including inflammation and rheumatoid arthritis. Ocular inflammation can be treated with a pharmaceutical composition containing the plant alkaloid tetrandrine (U.S. Pat. No. 5,627,195). U.S. Pat. No. 5,683,697 discloses a pharmaceutical composition having anti-inflammatory, anti-fever, expectorant or anti-tussive action, wherein the composition includes plant parts from the species *Melia, Angepica, Dendrobium, Impatiens, Citrus, Loranthus, Celosia, Cynanchum* and *Glehnia.* An herbal formulation comprising extracts of the roots, rhizomes, and/or vegetation of Alphinia, Smilax, Tinospora, Tribulus, Withania and Zingiber has been found to reduce or alleviate the symptoms associated with rheumatoid arthritis, osteoarthritis, reactive arthritis and for reducing the production of proinflammatory cytokines (U.S. Pat. No. 5,683, 698).

Based on the foregoing, there currently exists a need for antiinflammatory, analgesic and antipyretic herbal-based therapeutics which have low toxicity and few side effects. For example, there is a need for non-aspirin therapeutics for the treatment of fever, pain and inflammation associated with rheumatoid arthritis and osteoarthritis. The novel compositions of the present invention fulfill those requirements.

SUMMARY OF THE INVENTION

This invention comprises compositions for reducing inflammation, pain, and fever in a mammal, as well as methods of using such compositions in the treatment of these symptoms in animals.

The compositions of the present invention have analgesic, antipyretic, and antiinflammatory properties. More specifically, the compositions of the present invention can be used to alleviate symptoms associated with rheumatism and/or arthritis, especially those associated with rheumatoid arthritis and osteoarthritis.

The present invention provides compositions comprising talc, silkworm excrement, and ingredients of plants of species of the genera Stephania, Coix, Pinellia, Prunus, Phellodendron, Sophora, Tetrapanax, Stemona, Glycyrrhiza, Tripterygium, Forsythia and Siegesbeckia, wherein such compositions have analgesic, antipyretic, and antiinflammatory properties.

More specifically, the present invention comprises talc, silkworm excrement, and an extract from the seeds, roots, tubers, rhizomes, and/or vegetation of Stephania, Coix, Pinellia, Prunus, Phellodendron, Sophora, Tetrapanax, Stemona, Glycyrrhiza, Tripterygium, Forsythia and Siegesbeckia.

Even more specifically, the present invention provides compositions comprising talc, silkworm excrement and ingredients of plant species, wherein the plant ingredients include the root of Stephania, kernels of Coix, rhizomes of Pinellia, seeds of Prunus, bark of Phellodendron, roots of Sophora, stem of Tetrapanax, root tubers of Stemona, roots and/or rhizomes of Glycyrrhiza and Tripterygium, fruit of Forsythia and the above-ground parts of Siegesbeckia.

The present invention provides compositions comprising the active ingredients tetrandine, sophocarpidine, hydrochloric phellodendrine, triptolide and saponin, wherein the compositions have analgesic, antipyretic, and antiinflammatory properties.

One skilled in the art can easily make any necessary adjustments in accordance with the necessities of the particular situation. Further objects and advantages of the present invention will be clear from the description and examples which follow.

DETAILED DESCRIPTION OF THE INVENTION

I. GENERAL DESCRIPTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The current inventions in this application are in the fields of herbal-based pharmaceuticals and methods of using such medicines for the treatment of fever, pain and inflammation.

The compositions and methods of the present invention find particular application in the treatment of symptoms associated with various rheumatoid and rheumatoid-like diseases, especially osteoarthritis and rheumatoid arthritis.

Utilizing the results provided below, a skilled artisan can readily practice and develop the diagnostic, screening and therapeutic methods outlined herein and in the claims.

During a long-term rheumatoid disease research effort, the inventor of the present invention formulated numerous herbal-based medicinals and assessed their effectiveness in treating the fever, pain and inflammation associated with the disease. The compositions of the present invention were developed as a result of thousands of clinical assessments using various herbal-based medicines to treat rheumatoid symptoms. As discussed herein, the compositions of the present invention can be used instead of hormonal medicines or aspirin-based drugs to control the symptoms of rheumatoid arthritis during its active stages and to prevent articular deformity. The total effective rate of the composition approaches 97% in human clinical trials.

The composition of this invention comprises talc (($Mg_3$ ($Si_4O_{10}$)($OH$)$_2$), a silkworm excrement, and ingredients of plants of species of the genera Stephania, Coix, Pinellia, Prunus, Phellodendron, Sophora, Tetrapanax, Stemona, Glycyrrhiza, Tripterygium, Forsythia and Siegesbeckia. The individual components of the composition are described in greater detail in the following sections.

The Detailed Description and Examples provide detailed scientific results that can be used by a skilled artisan to prepare and administer the compositions of the present invention. The description of the present invention provided herein has been given for clearness of understanding only and no unnecessary limitations should be understood therefrom as modifications will be obvious to those skilled in the art.

II. COMPONENTS OF THE COMPOSITION

The composition of the present invention comprises talc, silkworm excrement and the dried plant parts of twelve different Chinese herbs. Each individual component is more clearly defined as set forth in the descriptions which follow.

A. Pulvis talci (talc)

General Description

The pulvis talci component of the composition is made with refined, purified, smashed/pulverized, and dried ore of talcum $((Mg_3(Si_4O_{10})(OH)_2))$. The dried ore of talcum utilized in the present invention was obtained from the Shandong and Jiangxi provinces of China.

Characteristics

White or nearly white color; fine texture; non-sandy powder, satiny feel, odorless, tasteless, and does not dissolve in water, dilute mineral acid, or alkali hydroxide.

pH test.

10 g of the substance is added to 50 ml of water, boiled for 30 minutes during which the evaporated moisture is replaced, then filtered. The filtrate shows neutral reaction upon conducting a litmus paper test.

Water-solubility.

50 g of the substance is added to 30 ml of the water, boiled for 30 minutes during which the evaporated moisture is replaced, cooled, filtered, and the residue from filtering is cleaned with 5 ml of water. The cleaning solution is combined with the filtrate and steam dried for 1 hour at 105° C. The residue will be 5 mg (0.1%) or less.

Acid solubility.

1 g of the substance is added to 20 ml of dilute hydrochloric acid, immersed for 15 minutes at 50° C., then filtered. 1 ml of dilute acid is added to 10 ml of the filtrate which is steamed dried and heated until constant weight is achieved. The residue will be 7.5 mg (1.5%) or less.

Ferric salt test.

10 g of the substance is added to 30 ml of water, heated and boiled for 30 minutes, the evaporated moisture is replaced, and the resultant mixture is cooled and filtered. 1 ml of dilute hydrochloric acid and potassium ferrocyandide are consecutively added to the filtrate. The resultant product will never show a blue color instantly.

Ignition weight:

The substance is heated until achieving a constant weight at 600–700° C. The total loss of weight in the resultant product is 5.0% or less.

Storage

The resulting substance is stored in air-proof containers.

B. Excrementum bombycis (silkworm excrement)

General Description

The excrementum bombycis component is made from the dried, solid feces excreted by *Bombyx mori* L., commonly known as the silkworm (family: Bombycidae). The silkworm is a moth caterpillar creamy white in color and approximately 7.6 cm long. The silkworm feeds chiefly on mulberry leaves and spins its cocoon from a silk fiber secreted by glands in its body. Either domesticated or wild silkworms can be used for preparing the excrementum bombycis used in the present invention. The silkworms utilized in the examples of the present invention were obtained from the Sichuan, Jiangsu, and Zhejiang provinces of China.

| Chemical Composition of Sample | |
| --- | --- |
| Organic substance: | 83.77–90.44% |
| Ash: | 9.56–16.23% |
| Nitrogen content: | 1.91–3.60% |
| Chlorophyl: | 1.6–2.4% |
| Pure chlorophyl: | 13.9% |
| Saponifying substance: | 48.9% |
| Phytol: | 0.25–0.29% |
| Non-Saponifying substance: | β-sitosterol 1.5% cholesterol ergosterol lupeol β-glucoscillaren free amino acid carotene. |

Extraction Process

Excrementum bombycis is placed into an extractor, 70% of ethanol is added, and the resultant mixture is heated under reflux. Ethanol is recovered and condensed under low-temperature and decompression until the specific density reaches 1.38 (thermal assay). The extract is then collected by vacuum drying.

Phototoxicity

Phototoxicity tests conducted using excrementum bombycis prepared from the excrement of silkworms fed an herbal diet demonstrate a slight, acceptable, phototoxic reaction. The phototoxicity tests are conducted based on the phototoxicity of sodium trichorophyllin and polymers thereof.

C. Herbal Components

The herbal components of the composition of the present invention are each provided herein. While the following examples provide preferred species and preferred plant parts to be used for each herbal component, as well as the geographic origin of the herbs used in the examples, one skilled in the art readily recognizes that alternative plant species and alternative plant parts, as well as alternative geographic sources for the plants, will satisfy the requirements of the composition. If herbs of an alternative species and/or plant part and/or plant origin were used to prepare the composition, then one skilled in the art could easily make any necessary adjustments in the preparation of the compostion to account for the lower or higher concentrations of any particular active ingredient.

Each of the following herbal components except leigongteng are included in the official medicaments described in the Chinese Pharmacopoeia (1990), which is herein incorporated by reference in its entirety.

1. Cortex phellodendri (Phellodendron bark)

General Description

The dried bark of *Phellodendron chinense* Schneid, or *Phellodendron amurense* Rupr. (family—Rutaceae) is used in the composition. The bark used in the examples of the present invention is from the Sichuan, Guizhou and Yunnan provinces of China, and Northeast China.

2. Semen *armeniacae* amarum (Prunus seeds)

General Description

The dried, ripe seeds of *Prunus armeniaca* L. Var. ansu Maxim., *Prunus sibirica* L., *Prunus mandshurica* (Maxim) Koehne, or *Prunus armeniaca* L. are used in the composition. (family—Rosaceae) are used in the composition. The seed used in the examples of the present invention were collected in the Heilongjiang, Liaoning, Jilin, and Hebei provinces of China.

3. Radix stemonae (Stemona tubers)

General Description

The dried root tuber of *Stemona sessilifolia* (Miq) Miq., *Stemona japonica* (B1.) Miq; or *Stemona tuberosa* Lour. (family—Stemonaceae) are used in the composition. The tubers used in the examples of the present invention were obtained in the Jiangsu, Anhui, Zhejiang, and Shandong provinces of China.

4. Semen coicis (Coix seeds)
General Description

The dried, ripe kernels of *Coix lacryma*-jobi L. Varmayuen (Roman) Stapf (family—Grarnineae) are collected in the autumn and dried. The kernels are separated from the shells, tawny seed coats and any impurities. The kernels used in the examples of the present invention were collected in the Jiangsu, Fujian, Hebei and Liaoning provinces.
Identification The starch grain turns brownish red when added to iodine test solution.

5. Rhizoma pinelliae (Pinellia tubers)
General Description

The dried stem tubers of *Pinellia ternata* (Thunb.) Breit. (family—Araceae) are used in the composition. The tubers used in the examples of the present invention were collected in the Sichan, Zhejiang, Anhui, and Jiangsu provinces of China.

6. Fructus forsythiae (Forsythia fruit)
General Description

The dried fruits of *Forsythia suspensa* (Thunb.) Vahl (family—Oleaceae) are used in the composition. The fruits used in the examples of the present invention were obtained from the Shanxi, Henan, Shaanxi and Shangdong provinces of China.

7. Radix *stephaniae tetrandrae* (Radix fangji) (Stephania roots)
General Description The dried root of the plant *Stephania tetrandra* S. Moore (family—Menispermaceae) are used in the composition. The roots used in the examples of the present invention are from the Anhui, Zhejiang, and Jiangxi provinces of China.

8. Medulla tetrapanacis (Tetrapanax stems)
General Description

The dried stem medullas of *Tetrapanax papyrferus* (Hook.) K.Koch (family—Araliaceae) are used in the composition. The plants used in the examples of the present invention were harvested in the Guizhou, Yunnan, Guangxi and Sichuan provinces of China.

9. Herba siegesbeckiae (Siegesbeckia plants)
General Description

The aerial part of *Siegesbeckia orientalis* L., *Siegesbeckia pubescens* Makino, or *Siegegsbeckia glabrescens* Makino (family—Compositae). The plants used in the examples of the present invention were obtained from the Jiangsu, Hubei, and Hunan provinces of China.

10. Radix *sophorae flavescentis* (Radix Kuh-seng) (Sophora roots)
General Description The dried root of *Sophora flavescens* Ait. (family—Leguminosae). The roots used in the examples of the present invention were obtained from the Shanxi, Henan, and Hebei provinces of China.

11. Radix et rhizoma tripterygii (Leigongteng) (Tripterygium roots and rhizomes)
General Description Leigongteng consists of the dried root and rhizome of *Tripterygium wilfordii* Hook. f. (family: Celastraceae). The roots are cylindrical, twisted, often connected to the aerial stems, 60 cm or more in length, and varying in thickness with diameters of approximately 0.5 cm–3 cm. The epidermis is rough, khaki or orange/yellow in color, with irregular longitudinal microgrooves and transverse tissues. The cortex is easy to peel off but it is difficult to break. The fracture surface displays a brownish violet or brown phloem, a yellowish white or light brown xylem, and is densely covered by pin holes. The rhizome is thick and strong, with a rough epidermis, often greyish brown in color. Leigongteng is slightly aromatic in odor, bitter and acrid in taste. Leigongteng has strong toxicity and care must be taken in the administration so as to prevent an overdose. The plants utilized in the examples of the present invention were obtained from the Zhejiang, Fujian, and Hubei provinces of China.
Processing The plant is gathered in the spring and autumn, cleaned, steeped in water for 4 to 6 hours, removed, and cut into thick slices, and dried out.
Identification Test Number 1.

50 ml of ethyl alcohol are added to 5 g of powdered leigongteng, the resultant mixture is refluxed on a water bath for one hour and filtered, the filtrate is evaporated to dryness, 5 ml HCL (0.1 mol/L) is added to dissolve the dried residue, and the resultant mixture is filtered. The filtrate is halved into two test tubes. To one tube are added 2 drops of potassium bismuth iodide TS and a yellow precipitate is produced. To the other tube are added 2 drops of potassium mercuric iodide TS and a white precipitate is produced. Next, 5 ml ethyl acetate are added to dissolve the acid-water-insoluble portion, the resultant mixture is filtered, 2 drops of 2% TS of 3.5-dinitrobenzoic acid and 2 drops of 5% TS of sodium hydroxide are added to the filtrate and a purplish red color appears.

Test Number 2.

100 ml anhydrous ethyl alcohol are added to 20 g of powdered Leigongteng, a reflux extraction is conducted for 1 hour, the resultant mixture is filtered, and the filtrate is evaporated to dryness. 3 ml ethyl acetate are added to dissolve the residue, then 3 g of neutral aluminum oxide are added, the resultant mixture is agitated thoroughly, and the solvent is allowed to volatilize out of the mixture. Next, the mixture is packed into a column of neutral aluminum oxide (internal diameter 1.5 cm dry packing with 11 g of neutral $AL_2O_3$) and eluted with 100 ml of chloroform. All of the chloroform is recovered from the eluate. 0.5 ml anhydrous ethyl alcohol is added to the residue to make a sample solution. Separately, triptolide (reference substance) is used to make a standard solution (0.5 mg/ml). According to the thin layer chromatography (see page 57 of the Appendices of Chinese Pharmacopoeia, Vol. One, 1990), 10 $\mu$l of the sample solution and 5 $\mu$l of the standard solution are separately added to same silica gel G plate, developed with a mixture of chloroform and ethyl ether (2:1), removed, and dried by airing; the plate is first sprayed with 2% alcoholic solution of 3.5-dinitrobenzoic acid, and then with 8% alcoholic solution of potassium hydroxide. The chromatogram produced by the sample solution must show the same purplish red spots as that shown by the standard solution in the corresponding areas.
Storage Store in dry, airy, mold and moth proof location.

12. Radix glycyrrhizae (Glycyrrhiza roots and rhizomes)
General Description

The dried root and rhizome of *Glycyrrhiza uralensis* Fisch., *G. inflata* Bat., or *G. glabra* L. (family—Leguminosae) are used in the composition. The roots and rhizomes used in the examples of the present invention are from the Inner Mongolia Autonomous Region and the Gansu, Shaanxi, Shanxi, and Oinghai provinces of China.

D. Proportion of Components in the Composition

The exact proportion of the Chinese herbs, pulvis talcum and excrementum bombycis in the composition will depend on the concentration of the active ingredients found naturally in each component. Using the guidance provided herein and a basic knowledge of drug preparation and pharmacology, one skilled in the art could easily adjust the proportions of the separate components of the composition so as to obtain a composition which has the therapeutic effects discussed and shown in the examples herein. The following discussion regarding the proportions of ingredients in the composition are provided as examples only and in no way limit the scope of the present invention from including any novel combination of the disclosed herbal and non-herbal components which have the intended effect of relieving the symptoms of pain, fever and inflammation, as discussed herein.

Composition Example 1. Based on the Percentages of the Herbal and Non-herbal Components.

| Ingredient | Percentage of Ingredient in the Composition |
| --- | --- |
| Pulvis talci | 1–10% |
| Excrementum bombycis | 5–15% |
| Cortex phellodendri | 5–15% |
| Semen armeniacae amarum | 5–15% |
| Radix stemonae | 1–10% |
| Semen coicis | 1–10% |
| Rhizoma pinelliae | 5–15% |
| Fructus forsythiae | 5–15% |
| Radix stephaniae tetrandrae | 5–15% |
| Medulla tetrapanacis | 5–15% |
| Herba siegesbeckiae | 1–10% |
| Radix sophorae flavescentis | 5–15% |
| Radix et rhizoma tripterygii | 1–15% |
| Radix glycyrrhizae | 5–15% |

Composition Example 2. Based on the Weight Ranges of Herbal and Non-herbal Components.

| Ingredient | Weight Range of Ingredient in the Composition |
| --- | --- |
| Pulvis talci | 100–120 g |
| Excrementum bombycis | 80–100 g |
| Cortex phellodendri | 80–100 g |
| Semen armeniacae amarum | 80–100 g |
| Radix stemonae | 80–100 g |
| Semen coicis | 170–190 g |
| Rhizoma pinelliae | 100–120 g |
| Fructus forsythiae | 170–190 g |
| Radix stephaniae tetrandrae | 80–100 g |
| Medulla tetrapanacis | 50–70 g |
| Herba siegesbeckiae | 170–190 g |
| Radix sophorae flavescentis | 80–100 g |
| Radix et rhizoma tripterygii | 50–70 g |
| Radix glycyrrhizae | 170–190 g |

Composition Example 3. Based on the Exact Weight of Herbal and Non-herbal Components.

| Ingredient | Weight of Ingredient in the Composition |
| --- | --- |
| Pulvis talci | 108 g |
| Excrementuin bombycis | 90 g |
| Cortex phellodendri | 90 g |
| Semen armeniacae amarum | 90 g |
| Radix stemonae | 90 g |
| Semen coicis | 180 g |
| Rhizoma pinelliae (prepared) | 108 g |
| Fructus forsythiae | 180 g |
| Radix stephaniae tetrandrae | 90 g |
| Medulla tetrapanacis | 60 g |
| Herba siegesbeckiae | 180 g |
| Radix sophorae flavescentis | 90 g |
| Radix et rhizoma tripterygii | 60 g |
| Radix glycyrrhizae | 180 g |

III. PREPARATION OF THE COMPOSITION

A. Preparation Procedure.

The composition of the present invention is made from twelve pure natural Chinese herbs, talc and silkworm excrement. The Chinese herbs are individually washed, dried and ground into fine powder, then extracted, for example, with medical ion exchange water and alcohol separately, and then mixed together. The resultant mixture is dried, smashed, screened, and then mixed with the talc and silkworm excrement. The final composition can be incorporated into any convenient mode of administration, with oral capsule intake being the preferred method of administration. Exemplified capsules each contain 0.4 g of the composition.

More specifically, the herb components radix *stephaniae tetrandrae* and radix et rhizoma tripterygii are ground into fine powder. The other ten herbs are decocted (i.e., boiled-down) with water twice: the first decoction uses water which weighs ten times as much as the total weight of the eleven herbs while the second decoction uses water which weighs eight times as much as the total herbal weight. The time for each decoction is two hours. The material resulting from the decoctions is then mixed and filtered so as to concentrate the filtrate to a heavy paste with a relative density of 1.30–1.35 (at 60–65° C.). Next, the powders of the pulvis talcum, excrementum bombycis, and the other two herbs are added to the heavy paste and the resultant product is mixed, dried, pulverized, sieved and mixed again until homogeneous. The resulting brown or greyish-brown powder, which is slightly bitter and sweet in taste, can be placed into capsules for oral administration to patients.

The primary active ingredients in the composition include tetrandrine, sophocarpidine, hydrochloric phellodendrine and saponin.

B. Quality Standards.

The quality standards for each of the herbs except radix et rhizoma tripterygii (leigongteng) are set forth in the Chinese Pharmacopeia (1990). The newly-devised assay test for radix et rhizoma tripterygii is provided in Assay Test Number 5.

1. Assay Test Number 1.

Add 25 ml of 70% ethyl alcohol to 2 g of the composition,, treat with ultrasonic irradiation for 1 hour, and then let stand for 12 hours. Pipet 10 ml of the supernatant liquid into an evaporating dish, evaporate to near dryness on a waterbath. Transfer the residue into a separating funnel with 20 ml of water, add 1 ml of concentrated ammonium TS, shake well, and then extract with chloroform for three times using 15 ml of chloroform each time, combine the extracts and recover the solvent chloroform. Add 2 ml ethyl alcohol to dissolve the residue to make up the sample or test solution.

Separately, use 0.5 g of radix *stephaniae tetrandrae* and 0.5 g of radix *sophorae flavescentis* to prepare two reference solutions by the same procedure.

In addition, produce two more reference samples by separately adding tetrandrine and matrine to ethyl alcohol (1 ml:1 mg).

According to the Chromatography Procedure on page 57 of the Appendices of Chinese Pharmacopoei (Volume One, 1990 edition), pipet 10 $\mu$L of the sample solution, and separately pipet 5 $\mu$l of the four reference solutions to the same plate of silica gel G. Use a mixture of petroleum ether (30–60° C.), ethyl acetate, and diethylamine (7:2:1) as developer to develop the chromatogram. Remove the plate, air dry, and spray with a dilute solution of potassium bismuth iodide. The chromatogram produced by the sample solution must show the same orange-yellow spots as that displayed by each reference solution in their corresponding areas.

2. Assay Test Number 2.

Add 20 ml of ammonium solution (1 mol/L) to 2 g of the powder, stir well, macerate for 10 minutes, and filter. Add 0.5 ml of concentrated sulfuric acid to the filtrate, agitate well, and filter. Add 2 ml of an alcoholic solution of ammonium (1 mol/L) to the residue to dissolve it. The resulting solution is the sample or test solution.

Separately, use 1 g of the reference "licorice" to make up a reference solution, using the same procedure as set forth in Assay Test Number 1 (see above).

Also, use "ammonium glycyrrhizinate" to make another reference solution by adding to it to ethyl alcohol (1 ml:1 mg).

According to the Chromatography Procedure on page 57 of the Appendices of Chinese Pharmacopoeia (Volume One, 1990 edition), pipet 10 $\mu$l of the sample solution, and separately pipet 4 $\mu$l of the two reference solutions and apply them to the same plate of silica gel GF254. Use a mixture of n-butanol, glacial acetic acid, and water (4:1:2) as a developer to develop the chromatogram. Remove the plate, air dry, and observe under an ultraviolet lamp (254 nm). The chromatogram produced by the sample solution must have the same quenching fluorescent spots as that of each reference solution in their corresponding areas.

3. Assay Test Number 3.

Add 10 ml of ethyl alcohol to 1 g of the composition and store overnight at room temperature. Filter the solution and evaporate the filtrate to dryness. Dissolve the residue with 1 ml ethyl alcohol to produce the sample or test solution.

Separately, use radix phellodendri to make a reference solution (Ref Sol. No. 1) by the same procedure as set forth in Assay Test Number 1 (see above).

Next, use berberine hydrochloride to make a second reference solution (Ref Sol. No. 2) by adding ethyl alcohol (1 ml:0.5 mg).

According to the Chromatography Procedure on page 57 of the Appendices of Chinese Pharmacopoeia (Volume One, 1990 edition), pipet 15 $\mu$l of sample solution, 3 $\mu$l of Ref. Sol. No. 1, and 1 $\mu$l of Ref. Sol. No. 2 to the same plate of silica gel G. Use a mixture of ethyl acetate, n-butanol, formic acid, and water as a developer (10:1:1:1) to develop the chromatogram. Remove the plate, air dry, and observe it under an ultraviolet lamp (365 nm). The chromatogram produced by the sample solution must show the same yellow fluorescent spots as that shown by each of the reference solutions in their corresponding areas.

4. Assay Test Number 4.

Place 65 g of the composition into a Soxhlet apparatus, add petroleum ether (30–60° C.) Q.S., run a hot reflux extraction for 3 hours, discard the solvent petroleum ether, let the remaining solvent volatilize away from the remaining product, and put the resultant product into a reflux extractor with chloroform and extract for an additional 3 hours. Next, recover the solvent chloroform from the extract, add 3 ml of ethyl acetate to the residue to dissolve it, and quantitatively transfer it into an evaporating dish. Add 3 g of neutral aluminum oxide, mix well, and volatilize the ethyl acetate. Next, place the resultant mixture into a column of neutral aluminum oxide (internal diameter 1.5 cm with 11 g of neutral $Al_2O_3$ packed by a dry process), elute with a mixture of chloroform and anhydrous ethyl alcohol (9:1), collect the eluate, and recover all the solvent from the eluate. Add 0.5 ml of anhydrous ethyl alcohol to dissolve the residue to produce the sample or test solution.

Separately, use radix et rhizoma tripterygii to make a first reference solution (Ref Sol. No. 1) by the same procedure as set forth in Assay Test Number 1 (see above).

Separately, dissolve triptolide in anhydrous ethyl alcohol to make a second reference solution (Ref. Sol. No. 2) (1 mg:0.5 mg).

According to the Chromatography Procedure on page 57 of the Appendices of Chinese Pharmacopoeia (Volume One, 1990 edition), pipet 10 $\mu$l of the sample solution and 3 $\mu$l of each of the reference solutions to the same plate of silica gel G, with a mixture of chloroform and ethyl ether (2:1) as developer to develop the chromatogram. Remove, air dry, spray with a 2% alcoholic solution of 3,5-dinitrobenzoid acid, and then spray with an 8% alcoholic solution of potassium hydroxide. Cover the chromatoplate with a glass pane and fix by adhesive tape on every side. According to the thin-layer scanning on page 57 of the Appendices of Chinese Pharmacopoeia (Volume One, 1990 edition), scan the chromatoplate at the wave length of $\lambda_S$=535nm and $\lambda_R$=700 nm. Separately measure the quantities and absorbencies of the sample and the reference, and make the appropriate calculations.

Triptolide ($C_{19}H_{24}O_6$) is the active component of leigongteng and can be quite toxic at higher concentrations. However, the amount of triptolide in raw leigongteng is very low, ranging from approximately 3.0–15.6 $\mu$g per gram of fresh weight. Using the methods of the present invention, the amount of triptolide contained in each 0.4 g of the composition (i.e., the usual amount in one capsule for oral administration) will be 0.2–1.0 $\mu$g per capsule. This low amount of triptolide in the compositions of the present invention is non-toxic and does not cause detrimental side effects as demonstrated by the animal tests and clinical studies reported herein.

5. Assay Test Number 5.

Use the sample solution and the two reference solutions prepared in Assay Test Number 5 (see above) for this assay.

According to the Chromatography Procedure on page 57 of the Appendices of Chinese Pharmacopoeia (Volume One, 1990 edition), pipet 10 $\mu$l of the sample solution and 5 $\mu$l of each of the reference solutions to the same plate of silica get G. Use a mixture of chloroform and ethyl ether as developer (2:1) to develop the chromatogram. Remove the plate and air dry. First spray the plate with a 2% alcoholic solution of 3,5-dinitrobenzoic acid and then spray it with an 8% alcoholic solution of potassium hydroxide. The chromatogram produced by the sample solution must show the same purple spots as that shown by the reference solutions in their corresponding areas.

6. Assay Test Number 6.

Place 5 g of the composition into a stoppered conical flask, add 50 ml of 70% ethyl alcohol, stopper, treat with ultrasonic irradiation for 1 hour, and let stand for 12 hours. Pipet 20 ml of the supernatant liquid into an evaporating dish, and evaporate using a waterbath until about 3 ml of the solutions is left. Transfer the resultant solution into a separating funnel with 50 ml water, add 2 ml of concentrated ammonium TS, shake well and then extract with chloroform five times, using 30 ml of chloroform for each extraction. Combine the dehydrated chloroform liquid with anhydrous sodium sulfate, recover all the solvent chloroform, dissolve the residue in anhydrous ethyl alcohol and quantitatively transferred into a 5-ml volumetric flask. Next, dilute to 5 ml with anhydrous ethyl alcohol, and shake well. The resultant solution is the sample or test solution.

To prepare a reference solution, add tetrandrine (the reference substance) to anhydrous ethyl alcohol (1 mg:0.5 mg).

According to the Chromatography Procedure on page 57 of the Appendices of Chinese Pharmacopoeia (Volume One, 1990 and edition), pipet 5 μl and 8 μl of the sample solution and 3 μl and 5 μl of the reference solution in a cross pattern on the same plate of silica gel G. Use a mixture of petroleum ether (30–60° C.), ethyl acetate, and diethylamine (7:2:1) as a developer to develop the chromatogram. Air dry, spray with a dilute solution of potassium bismuth iodide until wet and the spots appear clearly. Cover the chromatoplate with a glass pane and fix by adhesive tape on every side. According to the thin-layer scanning on page 57 of the Appendices of Chinese Pharmacopoeia (Volume One, 1990 edition), scan the chromatogram at the wavelengths $\lambda_S$=500 nm and $\lambda_R$=700 nm. Measure the quantities of absorbencies from the sample and the reference and make appropriate calculations.

The amount of radix *stephaniae tetrandrae* contained in each 0.4 g of the composition (i.e., the usual amount in one capsule used for oral administration) should not be less than 250 μg (based on tetrandrine ($C_{38}H_{42}N_2O_6$) being the principle component).

IV. STORAGE STABILITY OF THE COMPOSITION

Storage Stability Study. Three samples were obtained each from a different batch of the composition and placed in plastic bottles which were sealed tightly and left standing at room temperature for one year. The average room temperature at four different sampling times are shown in Table 1.

TABLE 1

Average room temperatures for four sampling times.

| Date | Temperature | Relative Humidity |
| --- | --- | --- |
| March, 1994 | 16.4° C. | 79.2% |
| June, 1994 | 29.2° C. | 76.5% |
| December, 1994 | 10.3° C. | 62.6% |
| March, 1995 | 17.0° C. | 79.3% |

The various tests and the test results for each of the three batches are shown in Tables 2, 3 and 4.

TABLE 2

Storability tests for Batch No. 940301. Mfg date: March 12, 1994.

| Standing time (Inspection date) Results Items | 0 month (Mar 94) | 3 months (June 94) | 9 months (Dec 94) | 12 months (Mar 95) |
| --- | --- | --- | --- | --- |
| Description | greyish-brown | as before | as before | as before |
| Identification | | | | |
| 1. Microscopic Identification | showing the feature stipulated | ditto | ditto | ditto |
| 2. Chromatographs of Fangji root & Kuh-seng root | positive reaction | ditto | ditto | ditto |
| 3. Chromatograph of Licorice | positive reaction | ditto | ditto | ditto |
| 4. Chromatograph of *Cortex phellodendri* | positive reaction | ditto | ditto | ditto |
| 5. Chromatograph of Leigongteng Determination | positive reaction | ditto | ditto | ditto |
| Water content % | 4.3 | 4.3 | 4.6 | 5.0 |
| Dissolution time (m) | 15 | 15 | 16 | 16 |
| Triptolide (μg/cap) | 0.45 | 0.43 | 0.41 | 0.41 |

TABLE 2-continued

Storability tests for Batch No. 940301. Mfg date: March 12, 1994.

| Standing time (Inspection date) Results Items | 0 month (Mar 94) | 3 months (June 94) | 9 months (Dec 94) | 12 months (Mar 95) |
| --- | --- | --- | --- | --- |
| Assay: | | | | |
| Tetrandrine (μg/cap) | 300 | 298 | 295 | 294 |
| Hygienic test | | | | |
| Bacteria | <10 | <10 | <10 | <10 |
| Fungi | <10 | <10 | <10 | <10 |
| Pathogenic bacteria | undetected | ditto | ditto | difto |
| Live acarids | undetected | ditto | ditto | ditto |

TABLE 3

Storability tests for Batch No. 940302. Mfg date: March 15, 1994.

| Standing time (Inspection date) Results Items | 0 month (Mar 94) | 3 months (June 94) | 9 months (Dec 94) | 12 months (Mar 95) |
| --- | --- | --- | --- | --- |
| Description | greyish-brown | as before | as before | as before |
| Identification | | | | |
| 1. Microscopic Identification | showing the feature stipulated | ditto | ditto | ditto |
| 2. Chromatographs of Fangji root & Kuh-seng root | positive reaction | ditto | ditto | difto |
| 3. Chromatograph of Licorice | positive reaction | ditto | ditto | ditto |
| 4. Chromatograph of *Cortex phellodendri* | positive reaction | ditto | ditto | ditto |
| 5. Chromatograph of Leigongteng Determination | positive reaction | ditto | ditto | ditto |
| Water content % | 5.8 | 5.8 | 6.0 | 6.1 |
| Dissolution time (m) | 18 | 19 | 19 | 20 |
| Triptolide (μg/cap) | 0.58 | 0.58 | 0.51 | 0.50 |
| Assay: | | | | |
| Tetrandrine (μg/cap) | 302 | 302 | 302 | 301 |
| Hygienic test | | | | |
| Bacteria | 50 | 50 | 50 | 100 |
| Fungi | <10 | <10 | <10 | <10 |
| Pathogenic bacteria | undetected | ditto | ditto | ditto |
| Live acarids | undetected | ditto | ditto | dittd |

TABLE 4

Storability tests for Batch No. 940303. Mfg date: March 9, 1994.

| Standing time (Inspection date) Results Items | 0 month (Mar 94) | 3 months (June 94) | 9 months (Dec 94) | 12 months (Mar 95) |
| --- | --- | --- | --- | --- |
| Description | greyish-brown | as before | as before | as before |
| Identification | | | | |
| 1. Microscopic Identification | showing the feature stipulated | ditto | ditto | ditto |

TABLE 4-continued

Storability tests for Batch No. 940303. Mfg date: March 9, 1994.

| Standing time (Inspection date) Results Items | 0 month (Mar 94) | 3 months (June 94) | 9 months (Dec 94) | 12 months (Mar 95) |
| --- | --- | --- | --- | --- |
| 2. Chromatographs of Fangji root & Kuh-seng root | positive reaction | ditto | ditto | ditto |
| 3. Chromatograph of Licorice | positive reaction | ditto | ditto | ditto |
| 4. Chromatograph of Cortex phellodendri | positive reaction | ditto | ditto | ditto |
| 5. Chromatograph of Leigongteng Determination | positive reaction | ditto | ditto | ditto |
| Water content % | 4.6 | 4.8 | 4.9 | 4.9 |
| Dissolution time (m) | 16 | 16 | 17 | 17 |
| Triptolide ($\mu$g/cap) Assay: | 0.53 | 0.51 | 0.48 | 0.45 |
| Tetrandrine ($\mu$g/cap) Hygienic test | 301 | 301 | 301 | 302 |
| Bacteria | <10 | <10 | <10 | 100 |
| Fungi | <10 | <10 | <10 | <10 |
| Pathogenic bacteria | undetected | ditto | ditto | ditto |
| Live acarids | undetected | ditto | ditto | ditto |

As demonstrated by the results presented above, the composition of the present invention is stable when stored for one year at room temperature in a closed plastic bottle. Every one of the tests conducted on the three batches of stored composition show no loss of quality when compared to freshly-prepared compositions.

V. PHARMACEUTICAL FORMULATIONS

The herbal components and non-herbal components of this invention can be used in the form of a medicinal preparation, for example, in solid, semi-solid or liquid form which contains the composition of the present invention, as an active ingredient, in admixture with an organic or inorganic carrier or excipient suitable for external, enteral or parenteral applications. The active ingredient may be compounded, for example, with the usual non-toxic pharmaceutically acceptable carriers for tablets, pellets, capsules, suppositories, solutions, emulsions, suspensions, and any other form suitable for use. Formulations of the present invention encompass those which include the exemplified carrier talc, as well as carriers other than talc such as water, glucose, lactose, gum acacia, gelatin, mannitol, starch paste, magnesium trisilicate, corn starch, keratin, colloidal silica, potato starch, urea and other carriers suitable for use in manufacturing preparations, in solid, semisolid or liquid form and in addition auxiliary, stabilizing, thickening and coloring agents and perfumes may be used.

For preparing solid compositions such as tablets or capsules, the principal active ingredients are mixed with a pharmaceutical carrier ( e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of a composition of the present invention, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as tablets, pills and capsules. This solid preformulation composition is then subdivided into unit dosage forms of the type describe d above containing 0.4 m g of the composition of the present invention, preferably in capsules. The tablets or pills of the novel composition can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate.

The liquid forms, in which the novel composition of the present invention may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the composition may take the form of tablets or lozenges formulated in conventional manners.

The active compounds may be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogert-free water, before use.

VI. EXAMPLES

A. Non-Human Animal Trials

Pharmacologic research shows that the composition of the present invention has an antiinflammatory effect on metatarsal enlargements as well as preventing or alleviating primary and secondary pathological conditions from arthritis of hamsters caused by administering a substance which causes inflammation. The composition of the present invention also provides dramatic antiinflammatory results due to carragheenin-induced edema in mice and albumin-induced edematous footpad in rats. In addition, the composition promotes blood flow and removes circulatory obstruction as shown by tests on the permeability of capillaries and modeling of granulomatosis in hamsters. Fever caused by a saccharomyces infection can be reduced for over 4 hours by taking the composition of the present invention. The composition of the present invention can also reduce writhing reaction created by chemical stimulus such as by acetic acid and also provide a painkilling effect.

General Experimental Method

The compositions used in these experiments were prepared by the Pharmaceutical Preparation Room of Taiyuan Rheumatoid Arthritis Hospital using the procedures outlined above. Distilled water was added to prepare a suspension of the density required for the tests.

Aspirin (99.6%) was manufactured by Nanjing Pharmacy. A 10% of gum acacia solution was added to prepare a suspension of the density required for the test.

Distilled water was used for the control groups.

The experimental mice and Wistar Rats were bought from the Animal Experiment Centre of Shanxi Medical College.

Animal Study 1

Inhibitory Action of the Composition on Primary Arthritis Caused by Freund's Complete Adjuvant Male rats were randomly divided into four groups of ten rats each, with the total weight of each group being 172.5±8.0 g. The perimeters of the rat hind paws were measured. Each group of rats was fed either water (control), aspirin (0.15 g/kg of body weight), or the composition of the present invention (either 1.5 g or 3.0 g/kg of body weight) by means of gastrogavage, once a day for 3 days. On the third day, 1 hour after the gastrogavage, 0.1 ml of Freund's complete adjuvant was intradermally injected into each rat's right hind paw to induce inflammation. The perimeters of the left and right hind paws were measured 2, 4, 6, 24, 48 and 72 hours after inflammation. As shown in Table 1, the composition of the present invention has an inhibitory action on the inflammation of primary arthritis caused by administration of Freund's complete adjuvanticity.

Animal Study 2

Inhibitory Action of the Composition on Primary Arthritis Caused by Freund's Complete Adjuvant Male rats were randomly divided into four groups often rats each, with the total weight of each group being 172.5±8.0 g. The perimeters of the left and right rat hind paws were measured. 0.1 ml of Freund's complete adjuvant was intradermally injected into each rat's right hind paw to induce inflammation. One week after injection of Freund's complete adjuvant, each group of rats was fed either water (control), aspirin (0.15 g/kg of body weight), or the composition of the present invention (either 1.5 g or 3.0 g/kg of body weight) by means of gastrogavage. The hind paws were observed and measured 1, 4 and 7 days after receiving treatments of either water, aspirin or the composition of the present invention. Results of the treatments were determined by measuring the degree of swelling of the injected versus non-injected hind paws, changes in body weight, the number of tubercles, and an overall visual score of the difference between the injected and non-injected paws. The visual score included observations on erythema of the ears and the swelling of the hind paws, anklejoints, and paw joints. The results are provided in Table 2. Compared with the control group, the swelling of the rats' paws after injection of the Freunds' complete adjuvant injection was significantly reduced for rats receiving either composition and compared favorably with the results of the aspirin treatment. The number of tubercles and the visual scores were also significantly lower for the rats treated with the composition as compared to the control group. No obvious changes were noted in rat body weight over the treatment regime.

TABLE 1

Inhibitory effect of the inflammation of primary arthritis caused by injection of Freund's complete adjuvant.

| Treatment | Dose g/kg | No. of Rats | Swelling Measurement ($\bar{x}$ mm ± SD) | | | | | |
| --- | --- | --- | --- | --- | --- | --- | --- | --- |
| | | | 2h | 4h | 6h | 24h | 48h | 72h |
| Control | | 10 | 6.4 ± 1.17 | 9.20 ± 0.92 | 6.50 ± 1.43 | 6.10 ± 0.88 | 6.00 ± 1.49 | 5.50 ± 2.37 |
| Composition | 3 | 10 | 4.40 ± 0.96 ** | 5.80 ± 1.03 ** | 5.40 ± 0.97 | 4.70 ± 1.34 ** | 5.40 ± 1.35 | 5.80 ± 2.75 |
| Composition | 1.5 | 10 | 4.60 ± 1.43 ** | 6.80 ± 1.62 ** | 5.50 ± 1.18 | 4.80 ± 1.03 ** | 5.90 ± 1.79 | 6.70 ± 1.95 |
| Aspirin | 0.15 | 10 | 2.40 ± 1.08 ** | 4.40 ± 1.57 ** | 5.30 ± 1.34 | 3.20 ± 092 ** | 5.01 ± 1.92 | 5.80 ± 1.75 |

Test. Compared with the Control. *P < 0.05. **P < 0.01

TABLE 2

Inhibitory effect on the inflammation of primary arthritis caused by injection of Freund's complete adjuvant.

| Treatment | Dose g/kg | No. of Rats | Swelling (x̄ mm ± SD) | Changes in Body Weight | | | No. of Tubercles | Visual Score |
|---|---|---|---|---|---|---|---|---|
| | | | | After 1 Day | After 4 Days | After 7 Days | | |
| Control | | 10 | 1.3 ± 0.67 | 165.3 ± 5.0 | 182.0 ± 11.2 | 200.4 ± 17.2 | 8 | 22 |
| Composition | 3 | 10 | 0.3 ± 0.94** | 174.8 ± 8.5 | 190.7 ± 14.2 | 210.3 ± 10.4 | 0 | 0 |
| Composition | 1.5 | 10 | 0.4 ± 0.87* | 175.3 ± 11.6 | 183.3 ± 15.5 | 209.0 ± 18.4 | 1 | 1 |
| Aspirin | 0.15 | 10 | 0.0 ± 0.57** | 174.5 ± 6.6 | 188.0 ± 5.0 | 215.3 ± 13.3 | 1 | 1 |

Test: Compared with the control. $P < 0.05$, **$P < 0.01$

Animal Study 3

Anti-inflammatory Function of the Composition on the Carragheenin Induced Edematous Footpad in Mice This test was conducted according to the procedure established by Xu-Shu-Yun, *Methodology of the Pharmacologic Experiments,* The People's Public Health Publishing House, 717 (1991). Male mice were randomly assigned to one of four groups of ten mice each, each group weighing 22.5±2.1 g. Each group of mice was fed either water (control), aspirin (0.15 g/kg of body weight), or the composition of the present invention (either 1.5 g or 3.0 g/kg of body weight) by means of gastrogavage, once a day for 8 days. On the eighth day, 1 hour after the gastrogavage, 0.1 ml of a 1.0% carrageenin solution was hypodermically injected into the right ankle joint. Using a volumometer, the volumes of the paw and ankle joints were measured 0.5, 1, 2, 3 and 4 hours after inflammation and the values were used to calculate a swelling value. As shown in Table 3, the composition of the present invention had a significant inhibitory effect on swelling and this positive effect lasted at least 4 hrs.

Animal Study 4

Inhibitory Action of the Composition on Albumin-induced Edema of Rat hind Paw This test was conducted according to the procedure established by Chen Qi, *The People's Public Health House,* 356 (1993). Rats were randomly divided into 4 groups of ten rats each, each group weighing 160.5±16.2 g. Each group of rats was fed either water (control), aspirin (0.15 g/kg of bodyweight), or the composition of the present invention (either 1.5 g or 3.0 g/kg of body weight) by means of gastrogavage, once a day for 3 days. On the third day, 1 hour after the gastrogavage, 0.1 ml of a 10.0% fresh egg white solution (diluted with normal saline) was hypodermically injected into the rat hind paw. The perimeters of the hind ankle joints were measured at different times in order to calculate degree of swelling. As shown in Table 4, the composition of the present invention had a significant effect on the degree of swelling when compared to the controls.

TABLE 3

Inhibitory effect of the composition on carrageen-induced edematous footpad in mice.

| Treatment | Dose g/kg | No. of Mice | Degree of Swelling of Hind Paw for a Given Time After Injection (x̄ ml ± SD) | | | | |
|---|---|---|---|---|---|---|---|
| | | | 0.5 hr | 1 hr | 2 hr | 3 hr | 4 hr |
| Control | | 10 | 0.10 ± 0.03 | 0.13 ± 004 | 0.08 ± 0.03 | 0.06 ± 0.05 | 0.04 ± 0.03 |
| Composition | 3 | 10 | 0.08 ± 0.02 | 0.11 ± 0.03 | 0.02 ± 0.02** | 0.02 ± 0.03* | 0.01 ± 0.02** |
| Composition | 1.5 | 10 | 0.09 ± 0.02 | 0.13 ± 0.03 | 0.05 ± 0.03* | 0.03 ± 0.03 | 0.01 ± 0.01** |
| Aspirin | 0.15 | 10 | 0.08 ± 0.03 | 0.12 ± 0.03 | 0.03 ± 0.02** | 0.01 ± 0.01* | 0.01 ± 0.0** |

Test: Compared with the control *$P < 0.05$, **$P < 0.01$

TABLE 4

Inhibitory effect on the albumin-induced edematous footpad.

| Treatment | Dose g/kg | No. of Mice | Degree of Swelling of Hind Paw for a Given Time After Injection ($\bar{x}$ ml ± SD) | | | | | |
|---|---|---|---|---|---|---|---|---|
| | | | 0.5 hr | 1 hr | 2 hr | 3 hr | 4 hr | 5 hr |
| Control | | 10 | 9.1 ± 0.9 | 8.2 ± 0.9 | 7.0 ± 0.9 | 5.3 ± 1.2 | 4.0 ± 0.7 | 4.5 ± 0.8 |
| Composition | 3 | 10 | 6.8 ± 1.1** | 4.7 ± 2.2** | 3.6 ± 1.7** | 3.0 ± 1.9** | 2.3 ± 1.4** | 2.5 ± 1.1** |
| Composition | 1.5 | 10 | 8.0 ± 0.7** | 6.0 ± 1.3** | 5.6 ± 1.8* | 3.4 ± 1.1** | 3.8 ± 1.0 | 4.1 ± 1.2 |
| Aspirin | 0.15 | 10 | 7.0 ± 0.8** | 5.1 ± 1.2** | 4.5 ± 1.5** | 3.4 ± 1.3** | 3.2 ± 1.0 | 3.2 ± 1.4* |

Test: Compared with the control. *P 0.05, **P < 0.01.

Animal Study 5

Inhibitory Effect of the Composition on Mice Capillary Permeability Induced by Glacial Acetic Acid This test was conducted according to the procedure established by Chen Qi, *The People's Public Health House*, 303 (1993). Mice were randomly assigned to one of 4 groups, each group having a total weight of 21.8±1.9 g and consisting of 5 male and 5 female mice each. Each group of mice was fed either water (control), aspirin (0.15 g/kg of body weight), or the composition of the present invention (either 1.5 g or 3.0 g/kg of body weight) by means of gastrogavage. One hour after the gastrogavage, a solution consisting of 0.5% Evans blue and (I.P.) 0.7% glacial acetic acid 0.1 ml/10 g (body weight) was hypodermically injected into the mice. I.P. densitometry values were collected 20 minutes after the injection. The results are presented in Table 5. Compared with the control group, the composition of the present invention significantly inhibited increased capillary permeability.

TABLE 5

Inhibitory effect of the composition on increased capillary permeability induced by I.P. 0.7 acetic acid in mice.

| Treatment | Dose g/kg | No. of Mice | Evans blue (densitometry) ($\bar{x}$ ± SD) |
|---|---|---|---|
| Control | | 10 | 0.479 ± 0.14 |
| Composition | 3 | 10 | 0.215 ± 0.08** |
| Composition | 1.5 | 10 | 0.233 ± 0.08** |
| Aspirin | 0.15 | 10 | 0.231 ± 0.07** |

Test: Compared with the control. **P < 0.01.

Animal Study 6

Inhibitory Effect of the Composition on the Hyperplasia of Connective Tissues

This test was conducted according to the procedure established by the Medication Dept. of the Public Health Ministry (*Collection of Guiding Principles on Western Medicine's Pre-Clinical Research*, 271 (1993)). Rats were randomly assigned to one of 4 groups, each group consisting of 8 rats with a total weight 157.8±9.0 g. The rats in each group were anesthetized, tiny incisions were cut on the left and right groins, and 10 mg of sterilized cotton was placed inside each cut. Each group of rats was fed either water (control), aspirin (0.15 g/kg of body weight), or the composition of the present invention (either 1.5 g or 3.0 g/kg of body weight) by means of gastrogavage, once daily for 8 days. On the day following the last gastrogavage, the cotton and any granuloma deposits thereon were removed from the incisions, dried at a temperature of 60° C. for 12 hours, after which they were individually weighed. The weight of the granuloma deposits was calculated by subtracting the dry weight of the removed cotton from the original weight of the cotton before insertion (i.e., 10 mg). The resulting values were converted into the dry weight of granuloma per 100 g of rat weight. The Inhibitory Ratio is calculated as follows:

Inhibitory Ratio=((control group average value−treatment group average)/(control group average))×100.

As shown in Table 6, the composition of the present invention had a significant inhibitory action on the hyperplasia of connective tissues (granulomatosis). The result provides scientific evidence that the composition of the present invention is useful for the treatment of acute rheumatoid arthritis.

TABLE 6

Inhibitory effect on granulomatosis induced by Cotton Pallet Method in rats

| Treatment | Dose g/kg | No. of Rats | Dry Weight of the granuloma (x-mg/100 ± SD) | Inhibitory rate % |
|---|---|---|---|---|
| Control | | 8 | 12.3 ± 1.3 | |
| Composition | 3 | 8 | 8.9 ± 1.0** | 27.64 |
| Composition | 1.5 | 8 | 10.0 ± 1.9* | 18.70 |
| Aspirin | 0.1 | 8 | 10.1 ± 1.6** | 17.89 |

Test: Compared with the control.
*P < 0.05, **P < 0.01.

Animal Study 7

Anti-pyretic Function of the Composition

This test was conducted according to the procedure established by Chen Qi, *The People's Public Health House*, 271 (1993).

The rats were randomly divided into 4 groups, each group weighing 210.0±10.9 g and consisting of 5 male and 5 female rats each. Rats were maintained in the test environmental conditions for 3 days during which their anal temperatures were recorded twice daily. On the fourth day the anal temperature was measured every half hour. Next, a 15% solution of fresh yeast suspension (2 ml/100 g) was injected into the back of each rat. Anal temperature was measured 4 hours later. The rats whose temperatures rose above 1° C.

were divided into 4 groups, each group consisting of 10 rats. Each group of rats was fed either water (control), aspirin (0.15 g/kg of body weight), or the composition of the present invention (either 1.5 g or 3.0 g/kg of body weight) by means of gastrogavage. Anal temperatures were determined 1, 2, 3 and 4 hours after the gastrogavage. As shown in Table 7, the mice that received the composition had lower temperatures than the control mice, with many of the differences being statistically significant. This result demonstrates that the composition of the present invention has an anti-pyretic (i.e., fever reduction) activity in rats with fever caused by yeast injection.

TABLE 8-continued

Analgesic action of composition on writhing reaction caused by injection of 0.5% of acetic acid

| Treatment | Dose g/kg | Mice | Writhing Quantity ($\bar{x} \pm SD$) | Analgesic Rate (%) |
|---|---|---|---|---|
| Aspirin | 0.2 | 20 | 24.4 ± 10.0** | 63.31 |

Test: Compared with the control **$P < 0.01$

B. Human Trials

TABLE 7

Anti-pyretic action of the composition on pyrexial rat caused by the injection of fresh yeast.

| Treatment | Dose g/kg | No. of Rats | Normal Body Temp. (°C.) | Body Temp. 4 hrs after injection with yeast (°C.) | Changes in Body Temperature after injection with yeast (°C. $\bar{x} \pm SD$) | | | |
|---|---|---|---|---|---|---|---|---|
| | | | | | 1 hr | 2 hr | 3 hr | 4 hr |
| Control | | 10 | 37.5 ± 0.5 | 39.0 ± 0.4 | 39.4 ± 0.5 | 39.5 ± 0.4 | 39.3 ± 0.4 | 39.4 ± 0.4 |
| Composition | 3 | 10 | 37.5 ± 0.1 | 39.0 ± 0.4 | 38.3 ± 0.5 ** | 38.0 ± 0.5 ** | 38.0 ± 0.7 ** | 37.9 ± 0.7 ** |
| Composition | 1.5 | 10 | 37.8 ± 0.2 | 39.1 ± 0.3 | 38.9 ± 0.5 * | 38.3 ± 0.8 ** | 38.4 ± 0.6 ** | 38.9 ± 0.9 |
| Aspirin | 0.15 | 10 | 37.5 ± 0.5 | 39.2 ± 0.4 | 37.9 ± 0.9 ** | 37.6 ± 09 ** | 37.8 ± 1.0 ** | 38.3 ± 0.7 ** |

Test: Compared with the control *$P < 0, 05$, **$P < 0.01$

Animal Study 8

Effect of the Composition on Writhing Activity

This test measures the analgesic action of the composition on writhing caused by injection of 0.5% acetic acid according to the procedure established by Chen Qi, *Methodology of Chinese Herbs Pharmacologic Research*, The People's Public Health Publishing House, 378 (1993).

The mice are randomly divided into 4 groups, each of which consists of 10 male and 10 female mice, with the total weight of each group being 20.9±1.1 g. Each group of mice was fed either water (control), aspirin (0.15 g/kg of body weight), or the composition of the present invention (either 1.5 g or 3.0 g/kg of body weight) by means of gastrogavage. One hour after the gastrogavage, a solution of (I.P.) 0.5% acetic acid (0.2 ml/20 g) was injected into the mice. The number of writhing reactions was counted during the 30 minutes immediately following the injection. As shown in Table 8, the composition of the present invention significantly reduced the writhing caused by injection of acetic acid into the mice.

TABLE 8

Analgesic action of composition on writhing reaction caused by injection of 0.5% of acetic acid

| Treatment | Dose g/kg | Mice | Writhing Quantity ($\bar{x} \pm SD$) | Analgesic Rate (%) |
|---|---|---|---|---|
| Control | | 20 | 66.5 ± 23.4 | |
| Composition | 3 | 20 | 27.5 ± 15.8** | 58.65 |
| Composition | 1.5 | 20 | 31.5 ± 17.6** | 52.63 |

Based on an ongoing series of pharmacological studies conducted by the China Academy of Traditional Chinese Medicine as well as an ongoing series of experimental studies with various herbal medicines throughout China, the composition of the present invention has been demonstrated to provide quick efficacy, a short treatment duration, no toxicity, and no adverse side effects. The results of the pharmacological study showed that the composition acts as an analgesic and a demulcent, relieves fever, reduces inflammation and promotes immuno-regulation. Significant efficacy has been achieved as a hormonal replacement for the treatment of rheumatoid arthritis, spondylarthritis ankylopoietica, systemic lupus erythematosus, erthema nodosum, scleroderma, Behcet's disease and Sjogren's syndrome. The composition is especially noted for controlling the effects of rheumatoid arthritis and for preventing joint deformity. Based on the observations of patients treated with the composition, including histopathological examinations on viscera, the composition caused no adverse effects to the hemogram or to liver/renal functions. In addition, no pathological problems were observed in any of the patients which were the result of administering the composition of the present invention. Considering clinical symptoms, signs, and lab indices, the composition has been demonstrated to markedly improve arthralgia and arthroncus and decrease inflammatory index. Based on the clinical studies, 97.2% of the patients had at least some relief of symptoms, while the overall curative rate was 38.52%. The dosage of the composition can be gradually reduced to a minimum maintenance dosage. Follow-up studies and clinical check-ups have shown that the post-curative effect is sustained and stable. To date, no cases of adverse reaction have been found.

The therapeutic composition of the present invention is normally administered using oral capsules each containing 0.4 g of the powder. Adults normally receive 3–5 capsules taken orally before meals three times daily. Based on their age and weight, children receive a lower dosage than adults.

Four typical cases are as follows:

Case Study 1. Patient 1—Age: 30; Sex: Male; Place of birth: Daxian, Sichuan; Occupation: peasant.

Condition before treatment: Overall swelling/painful joints for 18 years, both hands and elbows were deformed for 10 years, moved slowly with crutches.

Condition after treatment: After taking the composition for 30 days, the swelling and pain were completely relieved. Patient can now walk independently and take care of himself.

Case Study 2. Patient 2—Age: 29; Sex: Male; Place of birth: Huaiyuan, Anhui; Occupation: Worker Condition before treatment: Painful hip/knee joints for 15 years, rigid and stiff waist for 10 years, limited activity for 3 years, kyphotic bending. Patient height was 174 cm.

Condition after treatment: After taking the composition for 21 days, the hip/knee joint pains was completely relieved. Sixty days later, patient had could move flexibly and his fully-extended height reached 176 cm.

Case Study 3. Patient 3—Age: 47; Sex: Male; Place of birth: Kowloon, Hong Kong; Occupation: Businessman Condition before treatment: Spondylarthritis ankylopietica for 29 years. Despite an artificial joint replacement of his left hip and synovectomy of his right knee joint, his condition kept worsening. He moved with a wheelchair and drank via a hose, and his neck was stiff.

Condition after treatment: After taking the composition for 60 days, he could walk independently. Eight months later, he was able to hike and climb mountains.

Case Study 4. Patient 4—Age: 30; Sex: Female; Place of Birth: Taiyuan, Shanxi; Occupation: Unknown.

Condition before treatment: During her study in Japan, she had acute rheumatoid arthritis. Treatment of her conditions in Japan was not very effective. She return to China in a wheelchair.

Condition after treatment: After taking the composition for 20 days, she was well again and could walk up and down stairways. Sixty days later, she was able to walk normally.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

ADDITIONAL REFERENCES

1. Hang Lang, et al, Journal of Chinese Pharmacy University, 23(3):158 (1992).
2. Li Han-bao, et al, Journal of Chinese Materia Medica, 14(11):37 (1991).
3. Yu Liu-rong, et al, Journal of Chinese Herbs,19(2):18 (1988).
4. Guo Xin-fang, et al., Bulletin of Traditional Chinese Medicines, 11(8):38 (1986).
5. Hang Hai-lang, et al, Journal of Chinese Herbs, 19(4):19 (1988).
6. Peng Song, et al, Journal of Chinese patent medicines, 13(11):13 (1991).
7. The Chinese Pharmacopoeia, Volume One (1990).
8. Hang Qi-wei, et al, National Journal of Traditional Chinese Medicines, 18(11):669 (1993).
9. Chen Hao-an, et al, National Journal of Traditional Chinese Medicines, 18(4):232 (1993).
10. Ni Long, et al, Journal of Chinese Herbs, 25(5):245 (1994).
11. Pan Cheng-ri, et al, Selected works of the Annotation on the Chinese Pharmacopoeia (Volume One, 1990) (1993).

What is claimed:

1. A composition comprising talc, silkworm excrement, the root of Stephania, kernels of Coix, rhizomes of Pinellia, seeds of Prunus, bark of Phellodendron, roots of Sophor, stem of Tetrapanax, root tubers of Stemona, roots and rhizomes of Glycyrrhiza, roots and rhizomes of Tripterygium, fruit of Forsythia and the above-ground parts of Siegesbeckia.

2. The composition of claim 1 wherein the plants are *Stephania tetrandra, Coix lachryma-jobi, Pinellia ternata, Prunus mandshurica, Phellodendron amurense, Sophora flavescens, Tetrapanax papyriferus, Stemona japonica, Glycyrrhiza uralensis, Tripterygium wilfordii, Forsythia suspensa* and *Siegesbeckia glabrescens.*

3. The composition of claim 1 wherein the silkworm excrement is obtained from *Bombyx mori.*

4. The composition of claim 1 wherein the Prunus plants are selected from the group consisting of *Prunus armeniaca, Prunus sibirica,* and *Prunus mandshurica.*

5. The composition of claim 1 wherein the Phellodendron plants are selected from the group consisting of *Phellodendron amurense* and *Phellodendron chinense.*

6. The composition of claim 1 wherein the Stemona plants are selected from the group consisting of *Stemona japonica, Stemona tuberosa* and *Stemona sessilifolia.*

7. The composition of claim 1 wherein the Siegesbeckia plants are selected from the group consisting of *Siegesbeckia glabrescens, Siegesbeckia orientalis* and *Siegesbeckia pubescens.*

8. The composition of claim 1 wherein the Glycyrrhiza plants are selected from the group consisting of *Glycyrrhiza uralensis, Glycyrrhiza inflata* and *Glycyrrhiza glabra.*

9. The composition of claim 1 wherein the composition is in a form selected from the group consisting of powder, capsule, tablet, liquid, and caplet.

10. The composition of claim 9 wherein the composition is in the form of a capsule.

11. A method for reducing inflammation and pain in a mammal comprising administering a therapeutically effective amount of the composition of claim 9.

12. The method of claim 11 wherein the mammal is a human.

13. A method for alleviating symptoms associated with rheumatism comprising administering a therapeutically effective amount of the composition of claim 1 to a mammal.

14. The method of claim 13 wherein the rheumatism is rheumatoid arthritis.

15. A method for alleviating symptoms associated with arthritis comprising administering a therapeutically effective amount of the composition of claim 1 to a mammal.

16. The method of claim 15 wherein the arthritis is osteoarthritis.

17. A method for reducing fever in a mammal comprising administering a therapeutically effective amount of the composition of claim 1.

* * * * *